US006315782B1

(12) United States Patent
Chu et al.

(10) Patent No.: US 6,315,782 B1
(45) Date of Patent: *Nov. 13, 2001

(54) DEVICE AND METHOD FOR SEVERING LESIONS

(76) Inventors: Michael S. H. Chu, 121 Browne St., Brookline, MA (US) 02146; Yem Chin, 35 University Ave., Burlington, MA (US) 01803

( * ) Notice: Subject to any disclaimer, the term of this patent is extended or adjusted under 35 U.S.C. 154(b) by 0 days.

This patent is subject to a terminal disclaimer.

(21) Appl. No.: 09/351,292

(22) Filed: Jul. 12, 1999

Related U.S. Application Data

(63) Continuation of application No. 08/969,500, filed on Nov. 13, 1997.

(51) Int. Cl.[7] .................................................. A61B 17/12
(52) U.S. Cl. ........................................... 606/113; 606/139
(58) Field of Search .................................... 606/113, 114, 606/115, 139, 140

(56) References Cited

U.S. PATENT DOCUMENTS

| | | | | |
|---|---|---|---|---|
| 5,269,789 | * | 12/1993 | Chin et al. | 606/140 |
| 5,398,844 | * | 3/1995 | Zaslavsky et al. | 221/208 |
| 5,569,268 | * | 10/1996 | Hosoda | 606/140 |
| 5,624,453 | * | 4/1997 | Ahmed | 606/140 |
| 5,797,928 | * | 8/1998 | Kogasaka | 606/144 |
| 5,968,056 | * | 8/2000 | Chu et al. | 606/140 |
| 5,984,932 | * | 11/1999 | Yoon | 606/147 |
| 6,007,551 | * | 12/1999 | Peifer et al. | 606/140 |
| 6,099,535 | * | 8/2000 | Lamport et al. | 606/140 |

* cited by examiner

Primary Examiner—Jeffrey A. Smith
Assistant Examiner—Michael B. Priddy
(74) Attorney, Agent, or Firm—Kenyon & Kenyon

(57) ABSTRACT

A system for severing lesions within a living body includes a housing defining an interior tissue receiving chamber is coupled to the distal end of an endoscope. At least one snare extends around the ligating band supporting surface so that, when at least one ligating band is received around the ligating band supporting surface, drawing the at least one snare off the ligating band supporting surface releases a corresponding ligating band from the ligating band supporting surface. In addition, a method for severing tissue comprises the steps of introducing into the body an endoscope to which a housing defining an interior tissue receiving chamber is coupled, wherein at least one snare and at least one ligating band extend around the ligating band supporting surface and advancing the distal end of the endoscope into the body until the housing is located adjacent to a first portion of tissue to be severed. The first portion of tissue is then drawn into the interior chamber and a snare is drawn off the distal end of the housing to release a corresponding ligating band from the ligating band supporting surface so that the ligating band and the snare encircle the first portion of tissue.

20 Claims, 12 Drawing Sheets

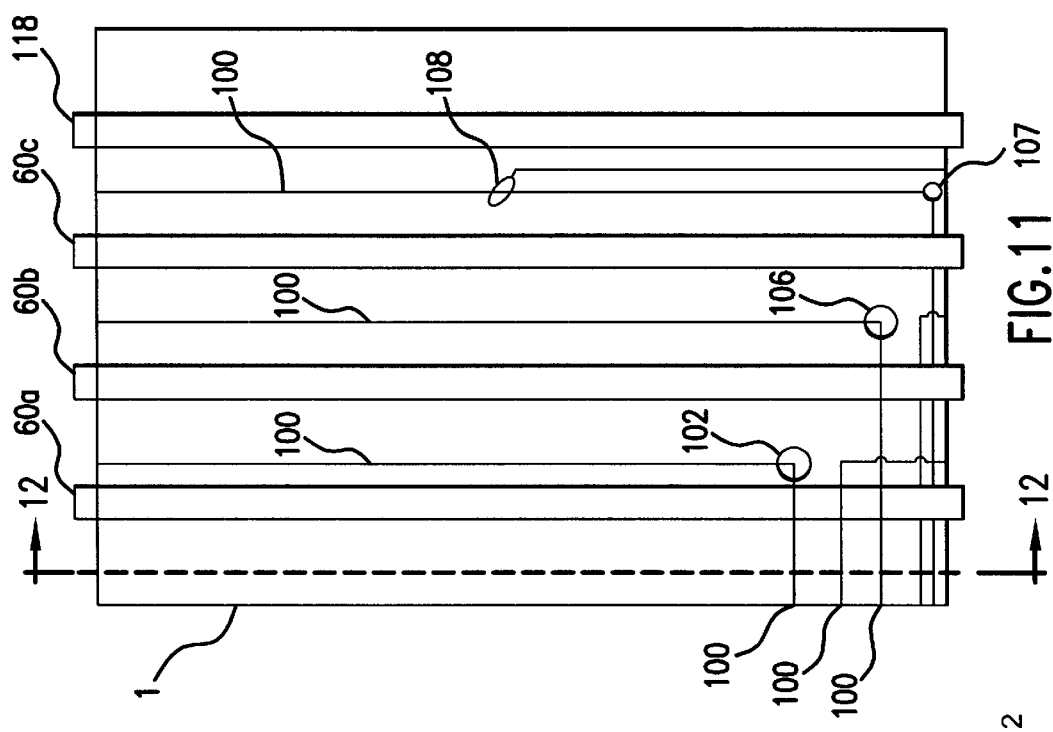
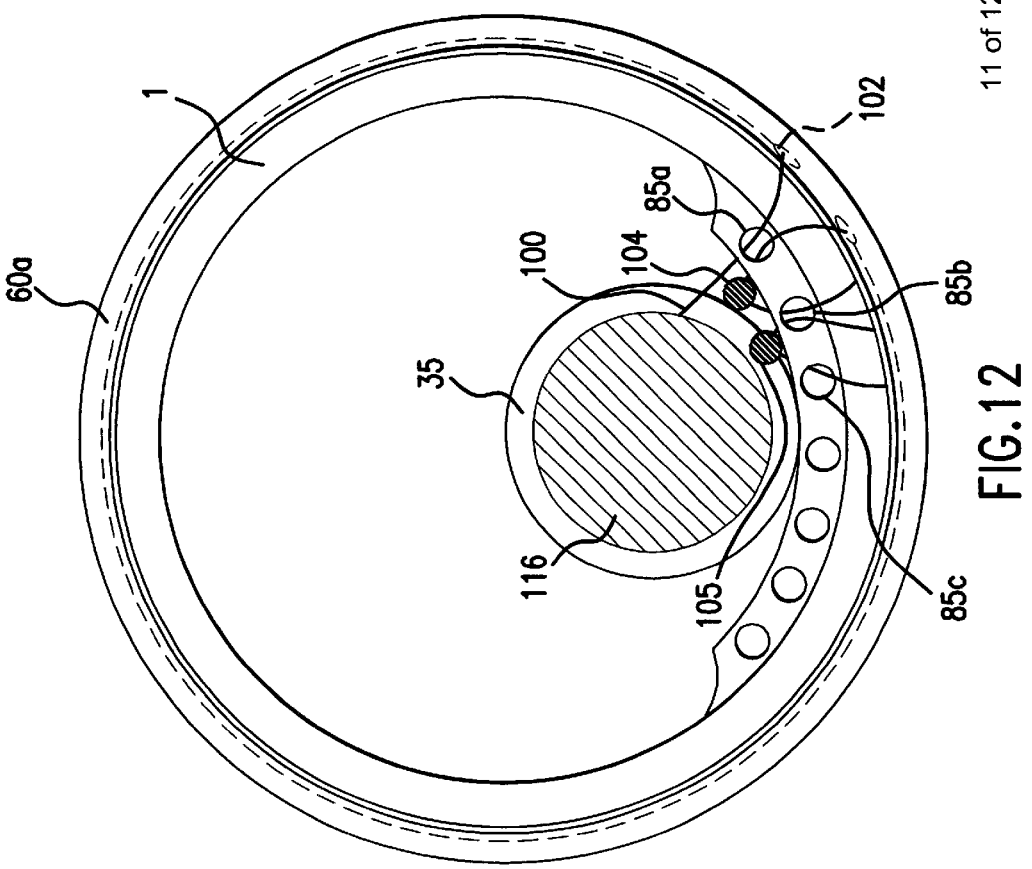

DEVICE AND METHOD FOR SEVERING LESIONS

The is a continuation of application Ser. No. 08/969,500, filed Nov. 13, 1997.

FIELD OF THE INVENTION

The present invention relates generally to the field of tissue ligation, and more particularly to an improved device and method for electrosurgically severing lesions.

BACKGROUND OF THE INVENTION

A wide variety of lesions, including internal hemorrhoids, polyps, and mucositis, may be treated by ligation. Ligating bands and severing snares are two types of devices commonly used to sever targeted lesions from surrounding tissue.

When performing ligating band ligation, a ligating band is initially placed over the targeted lesion or blood vessel section. As a ligating band is typically elastic in nature, the band must be stretched beyond its undeformed diameter before it can be placed over any tissue. After the tissue to be ligated has been drawn within the inner diameter of the ligating band, the band is allowed to return to its undeformed size and therefore apply inward pressure on the section of tissue caught within the band. The effect of the inward pressure applied by the band is to stop all circulation through the targeted tissue, thereby causing the tissue to die. In due course, the body sloughs off the dead tissue and allows it to pass through the body naturally.

Ligating band dispensing means are used to facilitate the placement of a single ligating band or a set of ligating bands over the targeted tissue. Two examples of ligating band dispensers are U.S. Pat. No. 5,356,416 to Chu et al. and U.S. Pat. No. 5,398,844 to Zaslavsky et al., both of which are incorporated herein by reference.

Alternately, a lesion may be removed through the use of an electrosurgical severing snare. Electrosurgery can be defined as the use of a radio frequency electric current to sever tissue or achieve hemostasis. A high radio frequency is used because a low frequency (i.e., below 100,000 Hz.) will stimulate muscles and nerves and could injure the patient. Electrosurgery is typically performed at frequencies of approximately 500,000 Hz., although frequencies as high as 4,000,000 Hz. may be used.

Medical diathermy is similar to electrosurgery in that radio frequency current is passed through the patient's body. The major difference between these two techniques is the density of the radio frequency electric current; the current density used in medical diathermy is kept low so as to reduce tissue heating and prevent necrosis.

There are three surgical effects that can be achieved with electrosurgery. These include electrosurgical desiccation, which is a low power coagulation caused without sparking to the tissue; electrosurgical cutting, where electricity sparks to the targeted tissue and produces a cutting effect; and electrosurgical fulguration, where electricity sparks to the targeted tissue without causing significant cutting.

The above-described surgical effects can be accomplished by using either a monopolar or bipolar output. For many applications, however, bipolar output is preferable because the patient return electrode (necessary in monopolar procedures and a common source of accidents) is eliminated, and any desiccation performed is extremely localized because, in a true bipolar operation, only the tissue that is grasped between the two electrodes is desiccated. Bipolar output, however, is poor for cutting or fulgurating, and thus monopolar tools remain commonplace. Severing snares, for example, are almost all monopolar instruments.

Three types of electrical current waveforms are typically used in electrosurgery. These include a "cutting" waveform, which cuts tissue very cleanly but may cause the incised tissue to bleed excessively; a "coagulating" waveform, which desiccates and fulgurates tissue without significant cutting; and a "blended" waveform, which is a cutting waveform that as a moderate hemostatic effect. A waveform's "Crest Factor" describes the degree of hemostasis that waveform can produce if properly applied.

To remove a lesion (or polyp) with an electrosurgical severing snare, a wire snare is looped around the targeted lesion. Next, the lesion is desiccated and is cut through electrosurgically. It is also possible to sever the lesion in a single step. By cutting with a "blended" current, it is possible to cut through a lesion in one pass without having to worry about bleeding. Alternately, a lesion may be cut through mechanically with a thin snare wire after the blood supply to the targeted tissue has been coagulated and the tissue softened by a desiccation current.

After the targeted lesion has been severed from the surrounding tissue, the severed tissue may be aspirated into an endoscope or similar device. In this manner, a sample may be retrieved for further study. Alternately, the severed tissue can be allowed to pass through the body naturally.

While bands are more effective in removing tissue while controlling bleeding, snares allow severed tissue to be retrieved and allow a user to cut deeper into the tissue, when increased suction is applied, to ensure, for example, that all diseased tissue is removed at once.

Electrosurgical cutting, however, is a difficult technique to master, especially when cutting large or sessile polyps. When using the "two step" cutting method (i.e., desiccation before cutting) whether the actual cut is to be made mechanically or electrosurgically, a precise amount of desiccation is required. If there is too little desiccation, the stalk may bleed when cut. If there is too much, the stalk may become too hard and dry to cut either mechanically or electrically. It is also exceedingly difficult to master "one step" cutting, which uses a blended current to ensure sufficient hemostasis. This is especially true when thick snare wires are used or a current with a high Crest Factor is applied. Often it will be very difficult to start cutting a given polyp. Thus, at times it may be desirable to use a pure cutting waveform to get the cut started. However, this may result in serious bleeding because the polyp has not previously been properly desiccated.

Currently, if it is desired to alternate between ligating band ligation and the use of electrosurgical snare, one or the other of these two types of instruments must be inserted through the working channel of an endoscope. Finishing with the first device, the user would have to withdraw this device from the endoscope before replacing it with the second device. In treatment of multiple lesions, for example, this process may need to be repeated several times, wasting the user's time, exposing the instruments to possible contamination during removal, and increasing the time and discomfort associated with the procedure.

SUMMARY OF THE INVENTION

The present invention is directed to a system for severing lesions within a living body which includes a housing defining an interior tissue receiving chamber coupled to the distal end of an endoscope. At least one snare extends around the ligating band supporting surface so that drawing the snare off the ligating band supporting surface releases a corresponding ligating band from the ligating band supporting surface.

In addition, the present invention is directed to a method for severing tissue comprising the steps of introducing into the body an endoscope to which a housing defining an interior tissue receiving chamber is coupled, wherein at least one snare and a corresponding ligating band extend around the ligating band supporting surface. The distal end of the endoscope is advanced into the body until the housing is located adjacent to a first portion of tissue to be severed. The first portion of tissue is then drawn into the interior chamber and a snare is drawn off the distal end of the housing to release the corresponding ligating band from the ligating band supporting surface so that the ligating band and the snare encircle the first portion of tissue. The user may then use the snare to sever an outer portion of tissue while the ligating band remains in place on an inner portion thereof.

BRIEF DESCRIPTION OF THE DRAWINGS

The invention will be more readily understood through the following detailed description, with reference to the accompanying drawings, in which:

FIG. 10b is a cross-sectional view of the connection of FIG. 10a taken along line A—A of FIG. 10a;

FIG. 11 shows a side view of a distal end of a fourth embodiment of the present invention in which each of the snares and pull wires is formed as a single wire;

FIG. 12 shows a cross-sectional view of the distal end of FIG. 11 taken along line 12—12 of FIG. 11.

DETAILED DESCRIPTION

Figure 1:
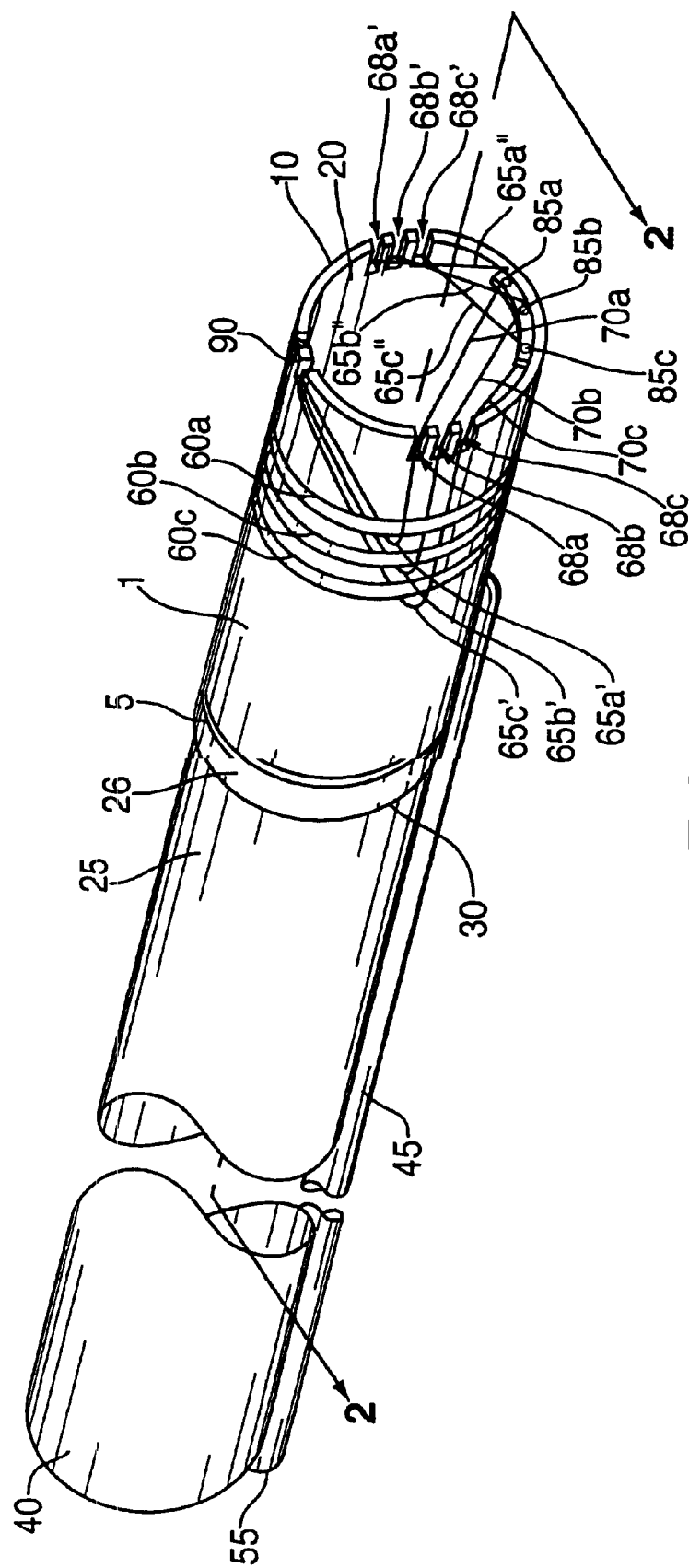
FIG. 1 is a perspective view of a first embodiment of the present invention.
Figure 2:
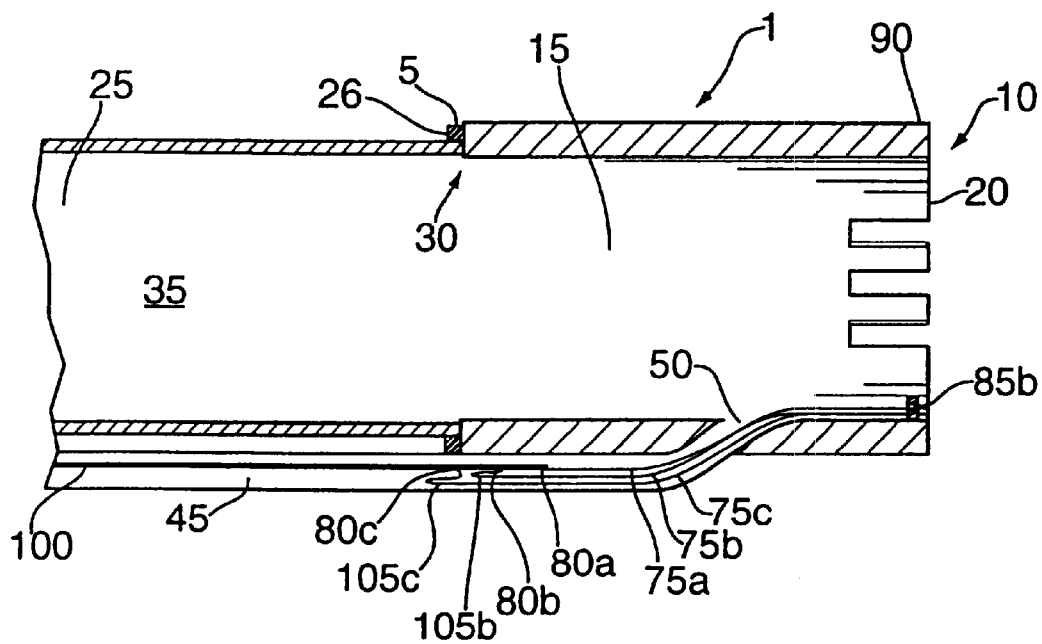
FIG. 2 is a sectional view of the first embodiment through the plane A—A.

As shown in FIGS. 1 through 6, the present invention comprises a housing 1, which has a proximal end 5 and a distal end 10. A lumen 15 extends between the proximal and distal ends 5 and 10, and may preferably have a generally circular cross-section. A distal aperture 20 is defined at the point where the lumen 15 exits the distal end 10 of the housing 1.

In operation, the housing 1 is attached to the working end 30 of an endoscope 25 by means, for example, of an elastic ring 26 coupled to a proximal end of the housing 1 as is known in the art. The endoscope 25 contains a working channel 35, which is defined within the endoscope 25 between a proximal end 40 and the working end 30. The working channel 35 is sized to allow the free passage of instruments from the proximal end 40, through the working channel 35 to the working end 30. In this manner, a user using the endoscope 25 can perform procedures on the patient in which the endoscope 25 and the housing 1 have been inserted.

The endoscope 25 may be any standard endoscope which is sufficiently long to reach the targeted lesions within the patient's body. In addition, the elastic ring 26 allows the housing 1 to be attached to endoscopes 25 of various sizes.

It may also be preferable to have an external channel 45 located outside the endoscope 25. As will be discussed later, a first embodiment of the invention includes a pull wire 100 that extends through an entrance port 55 of the external channel 45 to a position proximate an exit port 50 of the external channel 45. A portion of the pull wire 100 extends beyond the entrance port 55, so that a user may manipulate the pull wire 100 by applying a force on the exposed portion of the pull wire 100. By having the pull wire 100 pass through the external channel 45 rather than through the working channel 35 of the endoscope 25, a user may pass additional instruments, such as a needle 200 (seen in FIG. 6), through the working channel 35 of the endoscope 25 and the lumen 15 of the housing 1 without interfering or becoming entangled with the pull wire 100.

Figure 9:
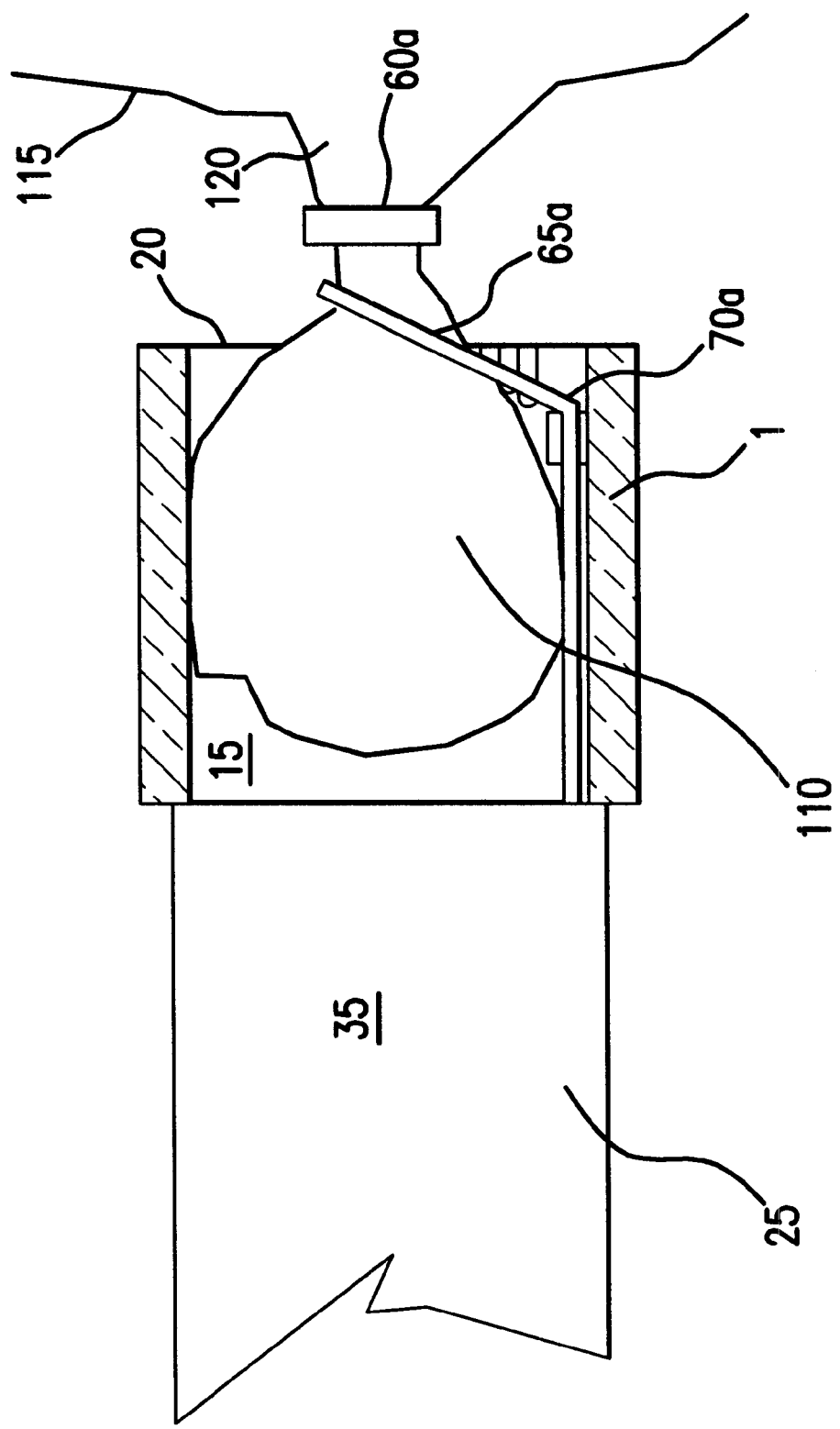
FIG. 9 is a cross-sectional view of a third embodiment of the present invention in which the pull wire 100 extends through the housing 1 from a proximal end to a distal end thereof.

Alternatively, as shown in FIG. 9 in the third embodiment, the pull wire 100 may extend through the working channel 35 of the endoscope 25 to directly enter the housing 1.

Figure 3:
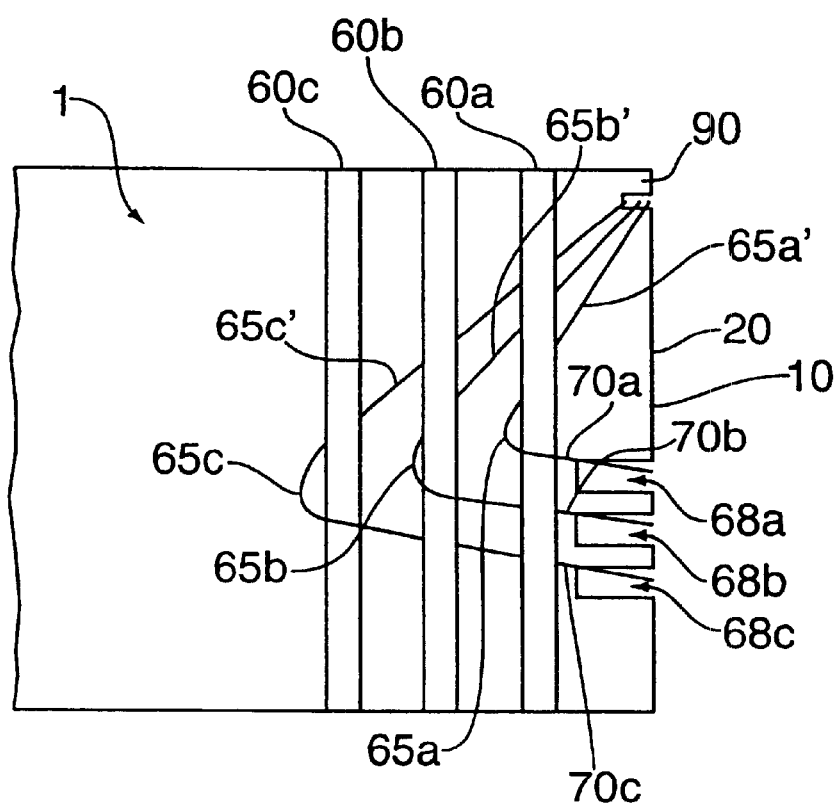
FIG. 3 is an enlarged detailed viewed of the distal end of the first embodiment through the plane A-B.

As seen in FIGS. 1 and 3, one or more ligating bands 60 are disposed about the housing 1 proximate the distal end 10 of the housing 1. For sake of illustration, the housing 1 is shown in FIG. 1 as holding three ligating bands 60a–c, although any number of ligating bands 60 may be used. In the first embodiment of the invention, for example, a total of 3–8 or more ligating bands 60 and a corresponding number of severing snares 70 may preferably be used. The numbering of ligating bands 60a–c corresponds to the order in which the ligating bands 60a–c will be dispensed from the housing 1. Ligating band 60a, for example, is located closest to the distal end 10 of the housing 1 and will therefore be the first ligating band 60 to be dispensed from the device.

Each ligating band 60a–c, is partially engaged by a portion of a distal loop 65a–c of a respective severing snare 70a–c. Each distal loop 65a–c of the severing snares 70a–c extends underneath each ligating band 60a–c that is more distal than the corresponding ligating band 60a–c which the respective severing snare 70a–c is designed to engage, the respective loop 65a–c then wraps over the respective band 60a–c and passes back under the more distal of the bands 60a–c to a snare catch 90. Distal loop 65c, therefore, passes underneath ligating bands 60a and 60b, before wrapping around the ligating band 60c and passing back underneath ligating bands 60a and 60b to the snare catch 90. Each severing snare 70a–c also includes a proximal end 75a–c, which is connected to the pull wire 100 at attachment points 80a–c.

The method by which a distal loop 65a–c engages a ligating band 60a–c will now be described with reference to distal loop 65c and the corresponding ligating band 60c. The distal loop 65c passes from the lumen 15 of the housing 1 through a snare port 85c. Alternately, a portion of the snare 70c exclusive of the distal loop 65c may pass through the snare port 85c, such that the entire distal loop 65c is initially outside the housing 1. First, the loop 65c of the proximal-most snare 70c is drawn out of the snare port 85c so that each of side sections 65c' and 65c▓ of the loop 65c passes through snare notches 68c and 68c' to extend along the sides of the housing 1. The ligating band 60c is then installed over the housing 1 and the side sections 65c' and 65c'' are drawn over the ligating band 60c to extend around a snare catch 90. Thereafter, the loop 65b of the snare 70b is drawn out of the snare port 85b, so that side portions 65b' and 65b▓ of the loop 65b pass through corresponding snare notches 68b' and 68b▓ to extend along the sides of the housing 1. The ligating band 60b is then installed over the housing 1, with the loop 65c and the side sections 65b' and 65b▓ on the distal side of the ligating band 65c. The loop 65b is then drawn over the ligating band 60b to extend around the snare catch 90 and the process is repeated with each successive ligating band 60 moving distally along the housing 1. Although FIG. 1 shows three snares 70 and three ligating bands 60, those skilled in the art will understand that any number of snares and ligating bands may be employed using this installation procedure.

All three distal loops 65a–c engage the snare catch 90. As seen in FIG. 3, distal loop 65c has been loaded onto snare catch 90 first, so that distal loops 65a and 65b can be disengaged from snare catch 90 without becoming entangled with distal loop 65c. The same goes for distal loop 65b with respect to distal loop 65a. Snare catch 90 is designed so that when a severing snare (e.g., 70a) is engaged, the ligating band 60a will be dispensed from the housing 1 over snare catch 90, without becoming entangled with any of the other distal loops 65b or 65c.

Figure 4:
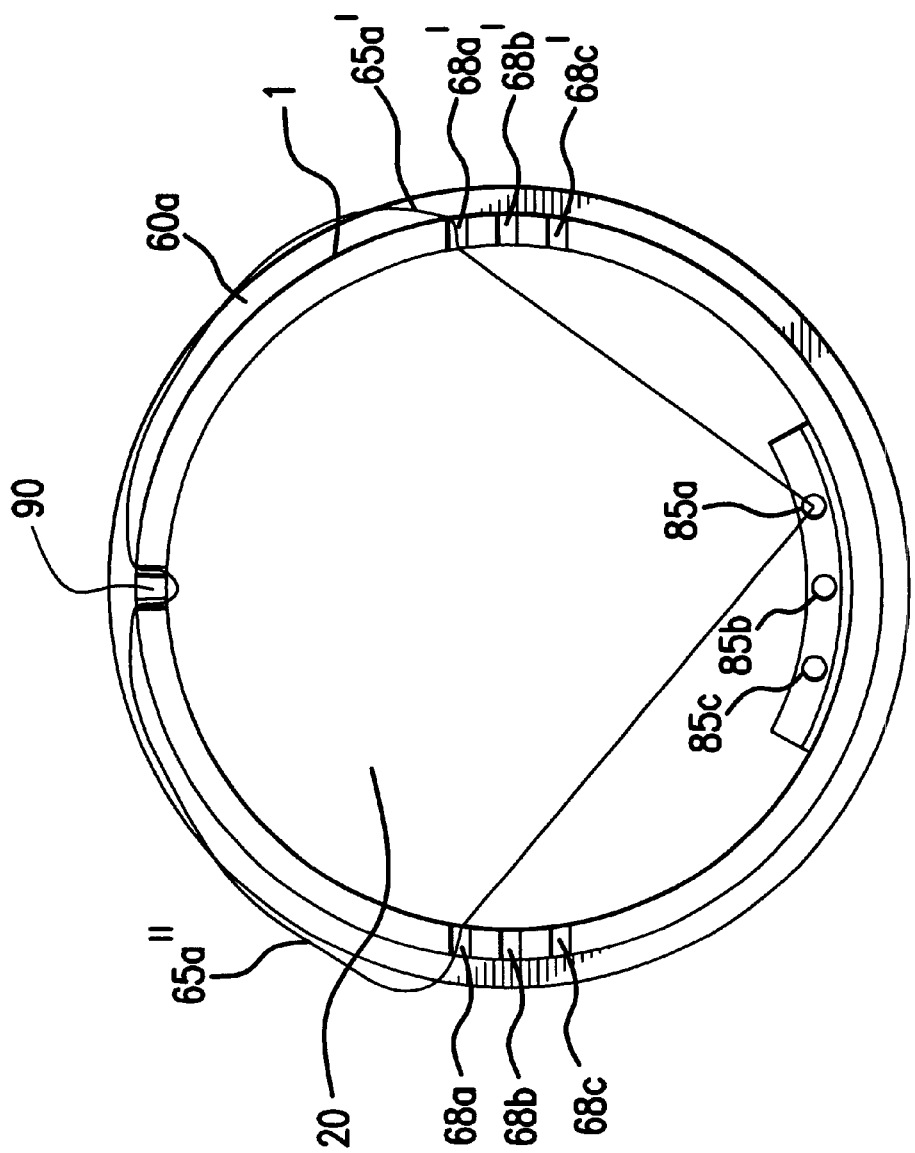
FIG. 4 is a plan view of the distal end of the first embodiment through a plane perpendicular to the plane A-B, and only showing one snare engaging a ligating band.

As seen in FIG. 4, each of the distal loops 65a–c (only distal loop 65a is shown) has a corresponding snare port 85a–c and a respective pair of snare notches 68a–c and 68a'–c'. In this manner, each distal loop 65a–c can be dispensed from the housing 1 without becoming entangled with any other distal loop 65a–c, provided the distal loops 65 are dispensed in the proper sequence (i.e., a, then b, then c). Also, snare ports 85a–c are preferably slightly recessed proximally from the distal aperture 20, to increase the angle at which the distal loops 65a–c engage snare notches 68a–c and 68a'–c'.

As mentioned earlier, the proximal ends 65a–c of the severing snares 70a–c are attached to the pull wire 100 at attachment points 80a–c at which electrically conducting portions of the distal loops 65a–c are exposed, while remaining portions of the distal loops 65a–c are electrically insulated except for distal end portions 82a–c. The severing snare 70a–c is attached to a pull wire 100 in such a manner so as to leave an amount of slack 105b and 105c in proximal ends 75b and 75c. This slack 105b–c is useful because when the pull wire 100 is initially engaged, tension is applied to the proximal end 75a of severing snare 70a first, without being applied to the proximal ends 75b–c of severing snares 70b–c. Instead, as the pull wire 100 moves proximally (to the left in FIG. 2), portions of the slack 105b–c are taken up before tension is applied to the proximal ends 75b–c. In this manner, the pull wire 100 may be used to manipulate each of the severing snares 70a–c independently of one another. The amount of slack 105b–c is preferably selected so that a respective ligating band 60 may be dispensed first by, e.g., one half turn of the crank 112 while a targeted lesion 110 may be severed by the corresponding snare 70 (e.g., snare 70a) by a further one half turn of the crank 112, after which the snare 70a is drawn completely through the snare port 85a into the housing 1, before the slack 105b associated with the next severing snare 70b has been taken up. Thus, the next snare 70b and the corresponding ligating band 60 will not be dispensed accidentally immediately after snare 70a has been deployed, (i.e., before the housing 1 is positioned adjacent to a second portion of tissue to be resected). Specifically, an amount of slack 105b will be selected so that the length of snare 70b is substantially equal to the length of the snare 70a plus a length equal to a full turn of the crank 112 and the amount of slack 105c will be selected so that the length of the snare 70c is equal to the length of the snare 70a plus two full turns of the crank 112.

Figure 10A:
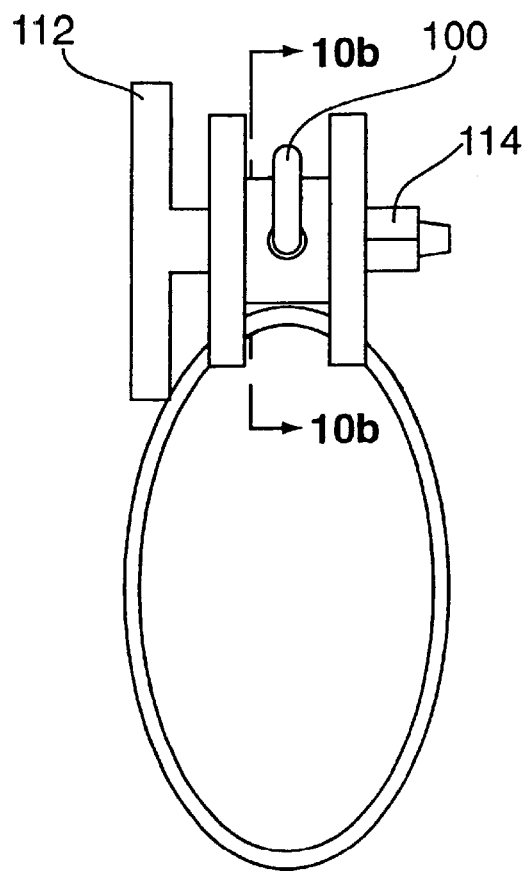
FIG. 10a is a side view of a connection between a pull wire, a pull wire crank and an r/f energy generator.
Figure 10B:
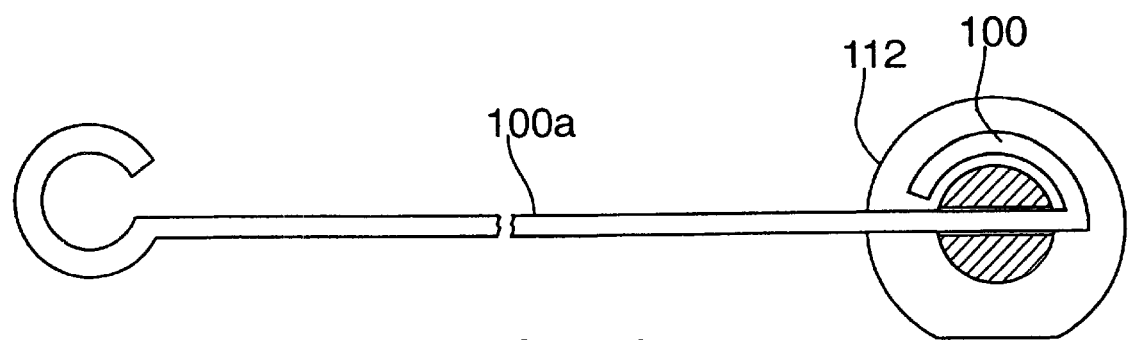

As is known in the art, a device such as a pull wire crank 112 as shown in FIGS. 10a and 10b, may be used to apply the necessary force to the pull wire 100 preferably via a stiffened, hooked pull wire 100a to dispense the ligating bands 60a–c and to manipulate the severing snares 70a–c. For example, the length of slack 105 may preferably be chosen so that a half turn of the pull wire crank 112 would release a ligating band 60 while a further one half turn of the crank 112 would draw the corresponding snare 70 into the housing 1 to sever the desired portion of tissue. The use of a slightly more rigid pull wire 100a also makes the threading of the pull wire 100 through the endoscope easier.

Figure 5A:
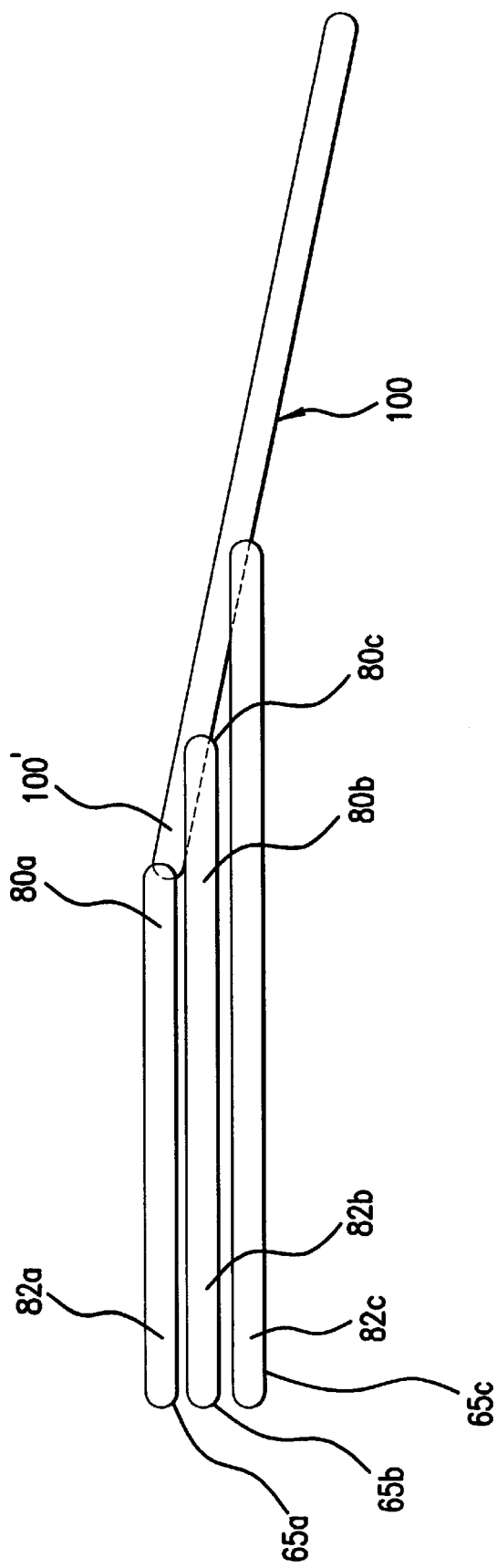
FIG. 5a is a side view of a pull wire/snare assembly used in the first embodiment of the invention.
Figure 5B:
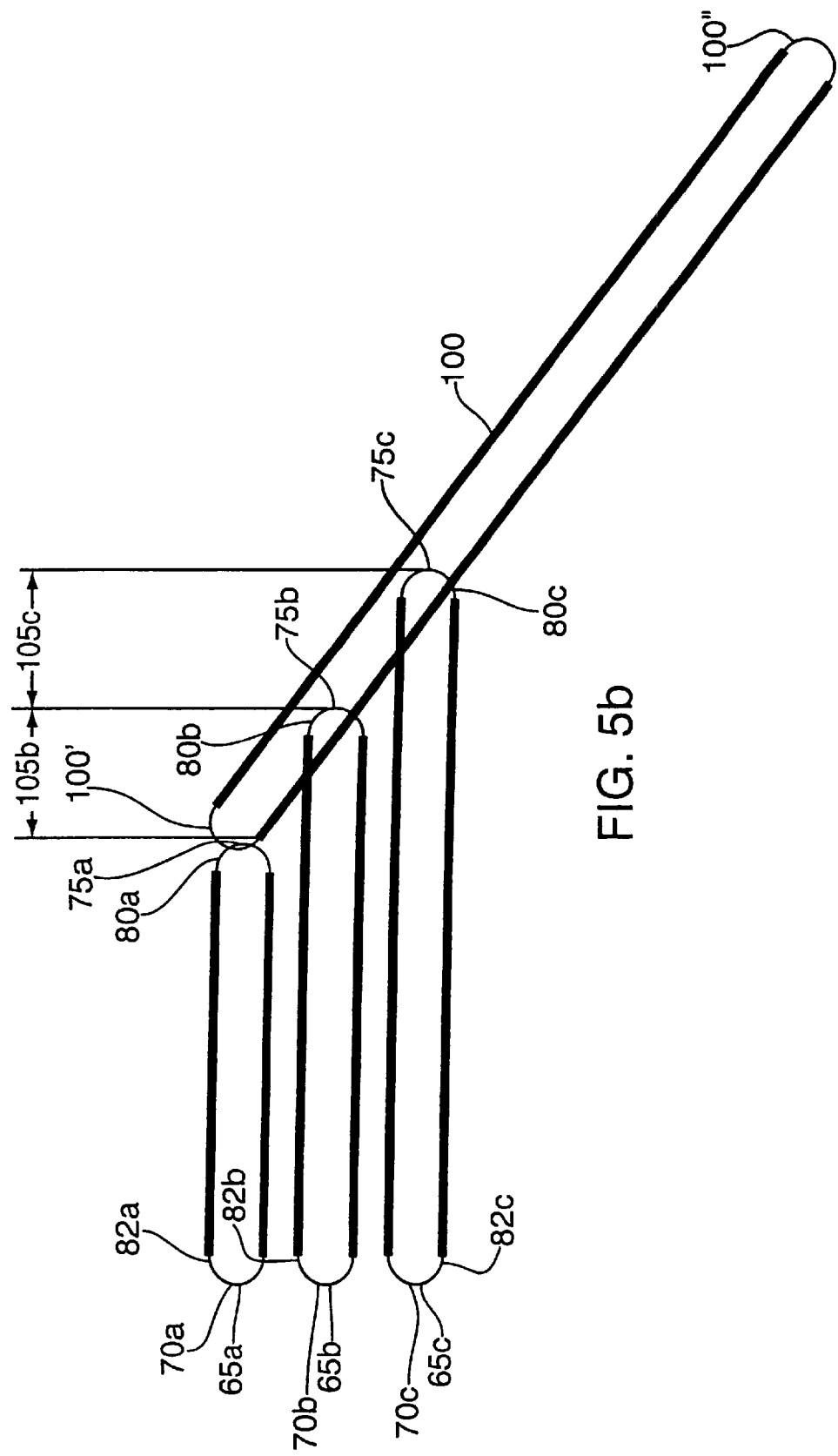
FIG. 5b is a side view of the pull wire/snare assembly of FIG. 5a with the loop 65a electrically coupled to the pull wire 100.
Figure 5C:
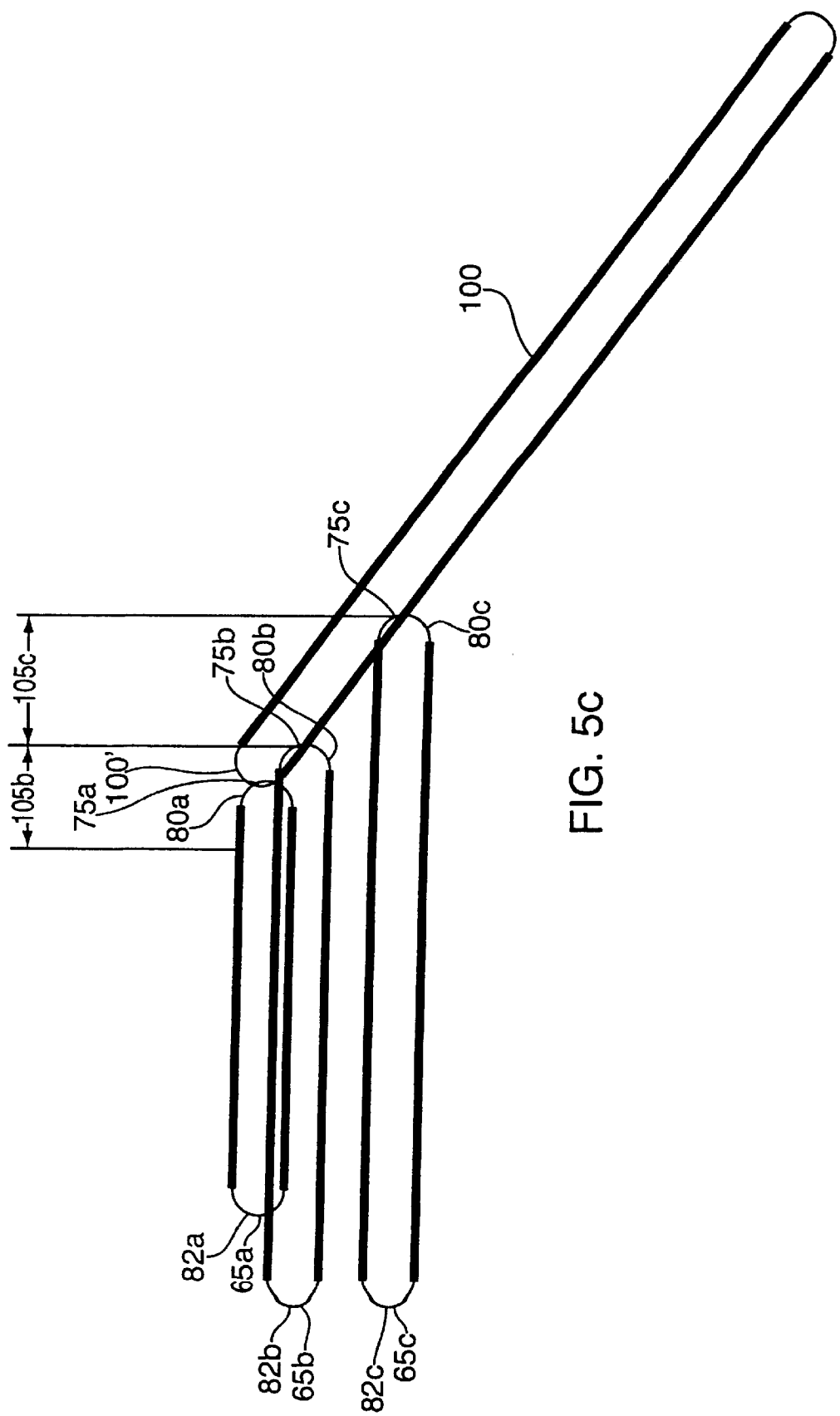
FIG. 5c is a side view of the pull wire/snare assembly of FIG. 5a with the loop 65b electrically coupled to the pull wire 100.

A detailed view of the attachment points 80a–c of the pull wire 100 is shown in FIGS. 5a–5c. As described above, in order to transfer r/f energy from the proximal end of the endoscope 25 to the snares 70, the pull wire 100 is formed of electrically conducting material which may be selectively electrically coupled to each of the snares 70a–c. This is accomplished through the action of slack 105b–c. Specifically, in an initial configuration, the pull wire 100 is electrically coupled to the loop 65a through contact between the contact portion 80a of the distal loop 65a and a distal contact portion 100' of the pull wire 100 in which the electrical insulation covering the remainder of a distal portion of the pull wire 100 is not present. Of course, an area on the proximal portion of the pull wire 100 also includes a proximal contact portion 100'' at which the electrically conducting wire is exposed for coupling to the hooked pull wire 100a which is, in turn, coupled to a source of r/f energy. Of course, this source of r/f energy may be activated and deactivated by a user of the device through, for example, a foot switch (not shown). As shown in FIGS. 5a–c, the distal loop 65b is longer than the distal loop 65a while the distal loop 65c is longer than the distal loop 65b, etc. Thus, the length of each of the distal loops 65 is increased in a regular progression from the loop 65a through the loop corresponding to the ligating band 60 installed proximal-most on the housing 1. As described above, this increase in length which forms the slack 105b–c ensures that only one of the snares 70 and the corresponding ligating band 60 will be activated at a time as the pull wire 100 is drawn proximally.

In addition, this slack allows the source of r/f energy (preferably coupled to the proximal contact area 100'' of the pull wire 100 via a plug 114 formed on the pull wire crank 112) to be coupled to the one snare 70 currently being manipulated by the user. As shown in FIGS. 5b and 5c, the pull wire 100 is formed as a loop of conducting material which extends through each of the loops 65a–c so that, as the pull wire 100 is drawn proximally the first loop 65a is drawn into the housing 1 and the distal contact portion 100' of the pull wire 100 advances relative to the contact portion 80b until the two contacting portions 80b and 100' come into contact with each other electrically coupling the loop 65b with the source of r/f energy. Similarly, after the user has finished with the snare 70b, drawing the pull wire 100 further into the housing 1 draws the contacting portion 80c further proximally until electrical contact with the distal contacting portion 100' is established. Thus, each of the loops 65 is first electrically linked to the source of r/f energy only as it is deployed from the housing 1, while the inactive loops 65 which remain in position around the housing 1 are decoupled from the source to prevent injury to surrounding tissue. Of course, the previously deployed snares 70 remain active, but these snares 70 are safely encased within the housing 1.

Figure 6:
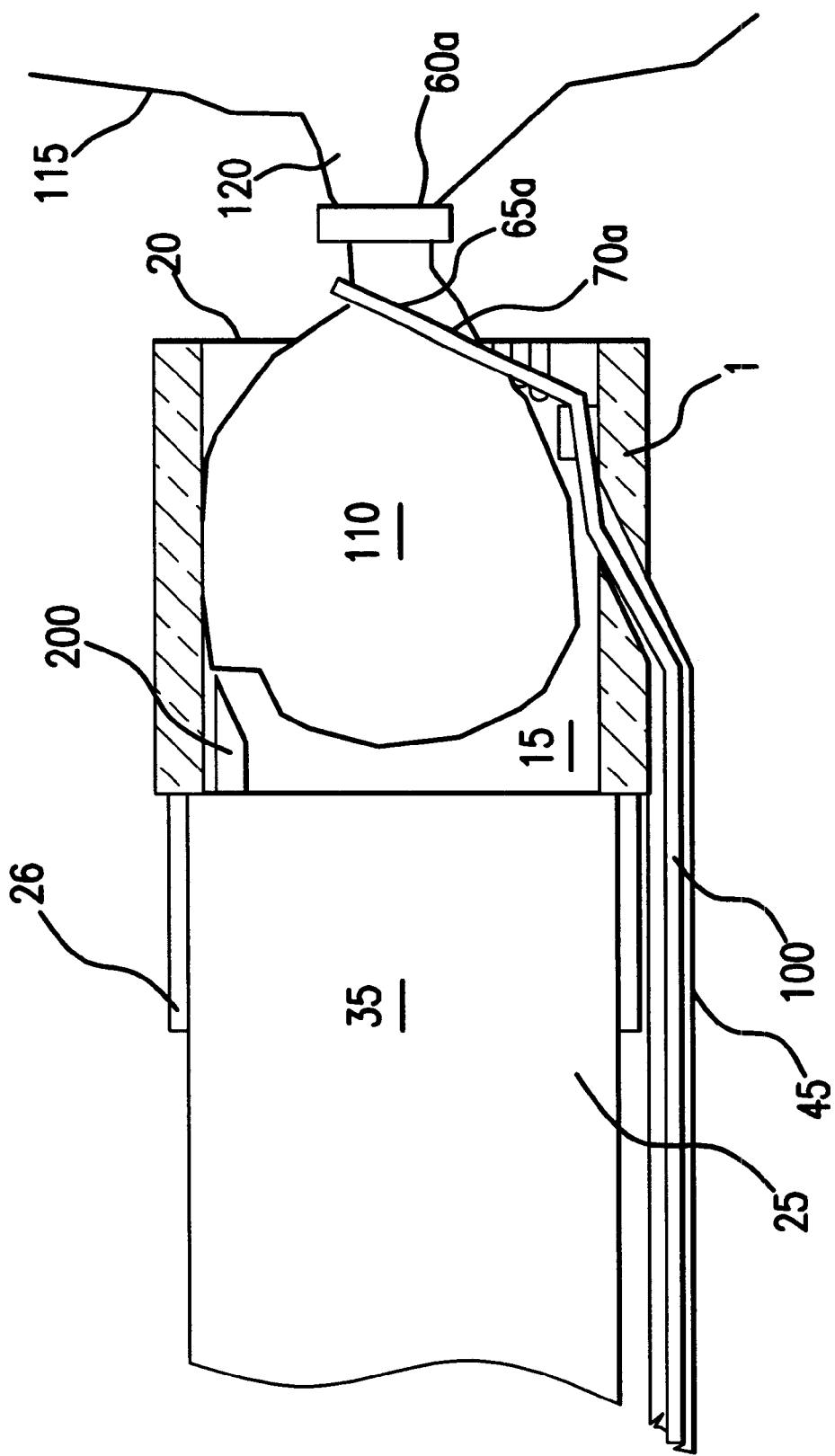
FIG. 6 is a perspective view of the first embodiment of the invention showing the invention being used to sever a lesion.

In use, as shown in FIG. 6 the endoscope is advanced until the distal end is adjacent to a lesion 110 to be ligated. The device may be positioned visually via an optical device (not shown) mounted in the endoscope. After visualizing the lesion 110, the user then decides whether to perform ligating band ligation, severing snare ligation, or a combination of the two on the targeted lesion 110. The user may also decide whether to engage the lesion 110 or the vessel wall 115 with a sclerotherapy needle 200, or other instrument, such as a forceps, basket, or cautery device, which may be passed through the working channel 35 of the endoscope 25 to the lumen 15 of the housing 1. Because the pull wire 100 preferably passes through the external channel 45, the working channel 35 is clear for the user to pass such additional instruments therethrough. The user may draw the lesion 110 into the distal aperture 20 under suction or with an instrument such as a forceps and may employ the forceps or suction after engaging the lesion 110 with a ligating band 60a, so that a tissue sample may be retrieved.

After the lesion 110 has been drawn within the housing 1, the user dispenses a ligating band 60a from the housing 1 by applying a force to the pull wire 100 (to the left in FIG. 6). The now-dispensed ligating band 60a engages lesion 110 and applies an inward force on the lesion 110, thereby restricting the flow of blood from the vessel wall 115 to lesion 110. In this manner, the desired level of hemostasis may be achieved and, eventually, the tissue dies and is sloughed off.

After the user has drawn the lesion 110 within the housing 1 and has dispensed the ligating band 60a from the housing 1, the distal loop 65a, which had engaged ligating band 60a about housing 1, is positioned about the stalk 120 of the lesion 110. Therefore, by drawing the pull wire 100 further proximally, the user pulls the distal loop 65a about the stalk 120, and may sever the lesion 110 either mechanically or electrosurgically. This severing step is preferably accomplished with one continual pull on pull wire 100, which, if the user elects to sever the lesion 110 electrosurgically, is done while simultaneously applying r/f energy to the snare 70a to facilitate cutting and cauterizing the targeted stalk 120.

If the user elects to use only ligating band ligation (i.e., not to use a severing snare), the user simply dispenses the ligating band 60a from the housing 1 after drawing the lesion 110 within the distal aperture 20 of the housing 1 by, for example, turning the crank 112 one half turn. Then, the user releases the tissue from the housing 1 and draws the snare 70 into the housing by a further one half turn of the crank 112.

After the lesion 110 has been severed from the vessel wall 115, the user may continue to apply suction through the working channel 35 to aspirate the lesion 110 through the lumen 15 into the working channel 35 of the endoscope 25. Alternately, the user may use suction to retain the lesion 110 within the lumen 15 of the housing 1 and then withdrawn the endoscope 25 and housing 1 from the patient. By proceeding in either of these manners, the user may obtain a sample of the lesion that has been severed for pathology evaluation. Alternately, the user may pass an instrument, such as a forceps, through the working channel 35 of the endoscope 25 and retrieve a sample of the lesion 110 for further study, either before or after the lesion 110 has been severed from the vessel wall 115.

Alternately, the user may disengage the suction means to allow the severed lesion 110 to pass through the body naturally. Whether the lesion is completely aspirated through the working channel of the endoscope 25, or allowed to pass through the body naturally, the user may proceed to treat additional lesions without removing the endoscope 25 from the patient. Of course, if the user desires to treat multiple lesions, the present device must be preloaded with a corresponding plurality of severing snares 70a–c and ligating bands 60a–c, rather than a single snare 70a and one ligating band 60a, as shown in FIG. 6. When the first lesion 110 has been severed, the user simply positions the housing 1 adjacent to a second lesion 110 and repeats the above described method.

Figure 7:
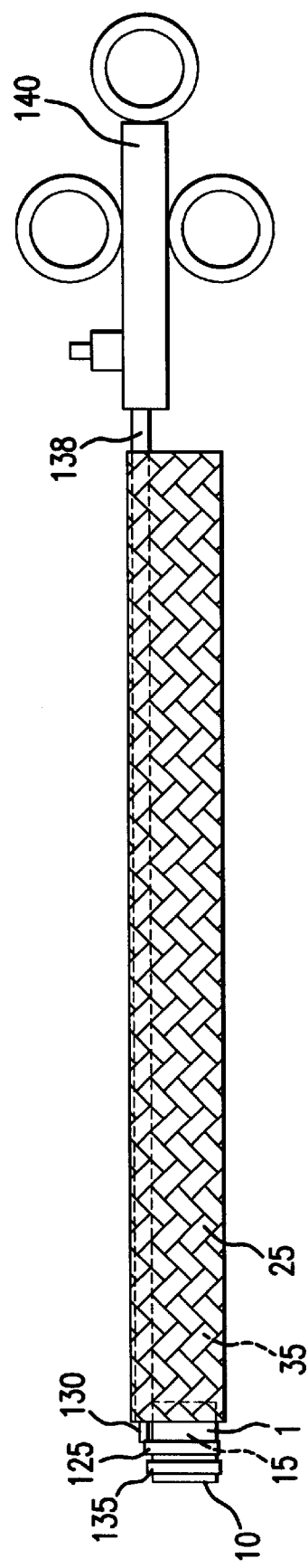
FIG. 7 is a cross-sectional view of a second embodiment of the invention.
Figure 8:
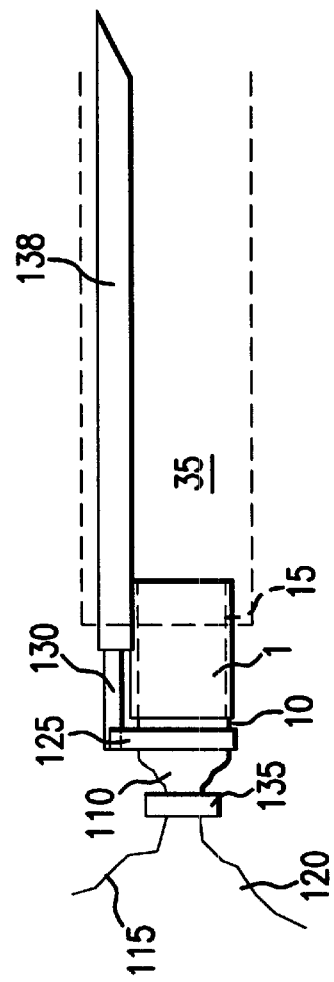
FIG. 8 is a cross-sectional view of the second as taken along line 2—2 of FIG. 1.

A second embodiment of the present invention is illustrated in FIGS. 7 and 8, in which a distal loop 125 of a severing snare 130 is positioned around the housing 1, but is located behind the ligating band 135 (i.e., is positioned proximally with respect to the band 135). The severing snare 130 passes along the endoscope 25 through a sheath 138, located outside the endoscope 25. By containing the severing snare 130 and the pull wire (not shown) within the sheath 138, the working channel 35 remains substantially clear so as to allow a user to pass an additional instrument, such as a needle (not shown) through the working channel 35 and through the lumen 15 without becoming entangled with the severing snare 130 or the pull wire.

By applying a force to the pull wire in the distal direction (i.e., to the left in FIG. 8), the distal loop 125 is moved toward the distal end 10 of housing 1 and dispenses the ligating band 135 from the housing 1. As discussed previously, if it is desired to engage a lesion 110 with the ligating band 135, the lesion is first suctioned into the lumen 15 of the housing 1. Then, with lesion 110 within the lumen 15, the ligating band 135 is dispensed to engage the stalk 120 of the lesion 110. By moving the pull wire further in the distal direction, the user can position the distal loop 125 around the desired portion of the lesion 110 and then retract the pull wire in the proximal direction to tighten the distal loop 125 about the lesion 110 and sever the lesion 110 mechanically or electrosurgically. Movement of the pull wire is preferably controlled by a handle 140 or similar means.

In the second embodiment of the invention, it is preferable to use a fairly sturdy distal loop 125 so that a ligating band 135 may be dispensed from the housing 1 when the pull wire is moved in the distal direction. That is, the pull wire must be stiff enough to carry a compressive load from the user to the distal loop 125 sufficient to overcome the friction forces maintaining the ligating band 135 on the housing 1.

Figure 13:
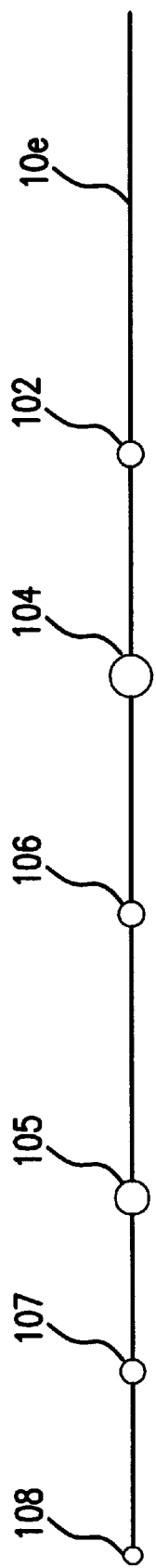
FIG. 13 shows a side view of a pull wire for use with the apparatus of FIG. 11.

An apparatus according to a fourth embodiment of the invention, as shown in FIGS. 11–13, is similar in construction to the previously described embodiments except that a single pull wire 100 is threaded through the device 1 to create a plurality of snares 70 which extend around the housing 1 abutting snares 70a–c which are located proximally of an optional proximal end wall 118.

As seen in FIG. 12, an instrument 116, e.g. a sclerotherapy needle, is present in the working channel 35 as well as the single pull wire 100 which extends through the working channel 35 in the space surrounding the instrument 116 to a first snare port 85a. The use of a single pull wire 100 allows the working channel 35 to comfortably accommodate an instrument 116 while providing the required control of the snares 70a–c. In addition, as no channels external to the endoscope are required with this apparatus, the cross-section of the device remains circular and the maneuverability of the device is enhanced.

Specifically as shown in FIG. 13, the pull wire 100 of this embodiment includes a first knot 102, a second knot 104, a third knot 106, a fourth knot 105, a fifth knot 107 and a loop 108. The pull wire 100 extends through the snare port 85a and underneath the ligating band 60a so that the knot 102 is located adjacent to a proximal edge of ligating band 60a. The pull wire 100 then wraps around the housing 1 to form snare 70a and passes back under the ligating band 60a and through the snare port 85a so that the knot 104 is located proximally of the snare port 85a. The knot 104 and the snare ports 85a and 85b are sized relative to one another so that the knot 104 may not pass through either of the snare ports 85a and 85b. The pull wire 100 extends from the knot 104 through the snare port 85b, passes underneath the ligating band 60a, under the snare 70a and under the ligating band 60b so that the knot 106 abuts a proximal edge of the ligating band 60b and wraps around the housing 1 to form snare 70b. The pull wire 100 wraps around the housing 1 and passes back under the ligating band 60b, under the snare 70a, under the ligating band 60a and reenters the snare port 85b so that the knot 105 is located on the proximal side of the snare port 85b. The knot 105 and the snare ports 85b and 85c are sized relative to one another so that the knot 105 may not pass through either of the snare ports 85b and 85c. Of course, those skilled in the art will understand that, although this embodiment is shown with 3 ligating bands 60a–c and 70a–c, this wrapping pattern may be repeated to create as many snares 70 as are desired until, after the pull wire 100 has passed under the proximal-most ligating band, 60c in FIG. 11, the pull wire 100 extends from the knot 107 abutting the proximal edge of the band 60c, around the housing 1 where, after encircling the housing 1, the snare 70c is formed by tieing a loop 108 around the preceding portion of the pull wire 100.

Those skilled in the art will understand, although FIG. 11 shows the ligating bands 60a–c spaced apart, that this is for illustration only. As the single pull wire 100 of this apparatus will transmit energy to all of the snares 70a–c when the source of r/f energy is engaged, the snares 70a–c should preferably be prevented from damaging adjacent tissue by abutting the ligating bands 60a–c against one another. Thus, the snares 70a–c will not contact the surrounding tissue.

In operation, when a portion of lesion tissue 110 is drawn into the housing 1 and it is desired to deploy the band 60a, the user turns the crank 112 one half turn as described above and the pull wire and the knot 102 are drawn distally across the housing 1, pulling the band 601 off of the distal end of the housing 1. Further rotation of the crank 112 will tighten the snare 70a around the lesion 110, eventually severing the tissue. Once the snare 70a has been fully retracted into the snare port 85a (knot 102 is sized so that it may pass through the snare port 85a), the pull wire 100 straightens out and portion of the pull wire 100 which formed the snare 70a no longer forms a loop. The amount of the pull wire 100 that needs to be taken up to fully retract the snare 70a also serves the purpose of preventing the premature release of the more proximal bands 60b–60c, etc. When a second portion of lesion tissue 110 has been located and drawn into the housing 1, the second ligating band 60b is released by a further one half turn of the crank 112. The knot 104 is drawn into the working channel 35 of the endoscope and knot 106 draws the band 60b off of the distal end of the housing 1. Thereafter, the operation of the snare 70b and any number of more proximally located snares 70 would be the same as that described for 70a and except that the proximal-most snare 70 will tighten like a noose as the pull wire 100 is drawn proximally, sliding through the loop 108.

Still other objects and advantages of the present invention will become readily apparent to those skilled in the art from the above-recited detailed description, wherein only preferred embodiments of the invention has been shown and described.

The description of the preferred embodiments is simply by way of illustration of the best mode contemplated for carrying out the invention. As will be realized, the invention is capable of other and different embodiments, and its several details are capable of modification in various respects, all without departing from the invention. Accordingly, the drawings and descriptions are to be regarded as illustrative in nature, and the scope of the invention is intended to be limited only by the claims appended hereto.

What is claimed is:

1. A system for severing lesions within a living body via an endoscope extending from a proximal end to a distal end of the endoscope, comprising:
    a housing having a proximal end configured to be coupled to the distal end of the endoscope, the housing defining an interior chamber for receiving a lesion therein and a ligating band supporting surface surrounding the interior chamber; and
    at least one lesion snare which, in an operative configuration, extends along a portion of the ligating band supporting surface distal of at least one ligating band received around the ligating band supporting surface.

2. The system according to claim 1, further comprising a snare aperture formed adjacent to a distal end of the housing, wherein a portion of the snare extends through the snare aperture.

3. The system according to claim 1, further comprising a pull wire extending from a proximal end of said pull wire which, in an operative configuration, is located outside the body to a distal end of said pull wire which is coupled to the at least one snare so that, drawing the proximal end of the pull wire proximally draws the at least one snare toward a distal edge of the ligating band supporting surface.

4. The system according to claim 1, further comprising a plurality of snares and a corresponding plurality of ligating bands received around the ligating band supporting surface.

5. The system according to claim 3, wherein the pull wire is coupled to a source of RF energy to selectively energize the at least one snare.

6. The system according to claim 3, further comprising a plurality of snares and a corresponding plurality of ligating bands received around the ligating band supporting surface, wherein the pull wire is coupled to a source of RF energy and is coupled to each of the plurality of snares so that, when the pull wire is drawn a first distance proximally, a first one of the snares is coupled to the source of RF energy, and when the pull wire is drawn a second distance proximally, a second one of the snares is coupled to the source of RF energy.

7. The system according to claim 1, wherein a channel extends through the endoscope to the distal end thereof so that when a distal end of the housing is positioned adjacent to a lesion, a force may be applied through the channel to draw the lesion into the interior chamber so that, when a ligating band is released from the ligating band supporting surface, the ligating band encircles the lesion.

8. The system according to claim 7, wherein force is applied through the channel via suction.

9. The system according to claim 7, wherein force is applied through the channel via a gripping device inserted therethrough.

10. The system according to claim 6, wherein the pull wire includes a first portion in which an electrically conductive material coupled to the source of RF energy includes no insulative cover and wherein each of the plurality of snares includes an electrically conductive tissue contacting portion coupled to the pull wire so that, as the pull wire is drawn proximally, the first portion of the pull wire is selectively electrically coupled each of the snares in turn to selectively couple the tissue contacting portion of each of the snares with the source of RF energy as the respective snare is released from the ligating band supporting surface.

11. The system according to claim 6, wherein the pull wire includes a first portion and a second portion in which an electrically conductive material is covered by insulative material and wherein each of the plurality of snares includes an intermediate portion located between a tissue contacting and proximal portions thereof, the intermediate portion including an insulative cover.

12. The system according to claim 1, wherein the interior chamber of the housing is sized so that a sclerotherapy needle may be passed therethrough from a proximal end to a distal end thereof.

13. The system according to claim 1, further comprising a pull wire extending from a proximal end which, in an operative configuration, is located outside the body to a distal end coupled to the at least one snare so that, drawing the proximal end of the pull wire proximally draws the at least one snare toward the distal edge of the ligating band supporting surface, wherein a channel extends through the endoscope to the distal end thereof so that when a distal end of the housing is positioned adjacent to a lesion, a force may be applied through the channel to draw the lesion into the interior chamber so that, when a ligating band is released from the ligating band supporting surface, the ligating band encircles the lesion and wherein the pull wire extends through the channel to the distal end of the endoscope.

14. The system according to claim 4, wherein the plurality of snares are formed, together with the pull wire, from a single strand.

15. The system according to claim 14, wherein the single strand is formed of an electrically conducting material.

16. A method for severing tissue within a living body comprising the steps of:
    introducing into the body a distal end of an endoscope to which a proximal end of a housing is coupled, the housing defining an interior chamber for receiving tissue therein and an outer ligating band supporting surface surrounding the interior chamber, at least one snare extending along a portion of the ligating band supporting surface distal of at least one ligating band;
    receiving a first portion of tissue within the interior chamber; and
    moving the at least one snare off a distal end of the housing to release the at least one ligating band from the ligating band supporting surface so that the at least one ligating band and the at least one snare encircle the first portion of tissue.

17. The method according to claim 16, wherein the at least one snare is received around the ligating band supporting surface so that, as the snare is drawn off the ligating band supporting surface, the at least one ligating band precedes the at least one snare and is released from the ligating band supporting surface before the at least one snare, further comprising the step of severing, by means of the at least one snare, a first part of the first portion of tissue so that the at least one ligating band remains in place around a remaining part of the first portion of tissue.

18. The method according to claim 17, wherein the step of severing by means of the at least one snare comprises supplying RF energy to the snare.

19. The method according to claim 16, wherein a plurality of snares and a corresponding plurality of ligating bands are received around the ligating band supporting surface so that, as a respective snare is drawn off the ligating band supporting surface, a corresponding ligating band is released from the ligating band supporting surface, further comprising the steps of:
    after a first one of the plurality of ligating bands has been released from the ligating band supporting surface;
    receiving a second portion of tissue within the interior chamber;
    urging a second snare off the distal end of the housing to release a second ligating band from the ligating band supporting surface so that the second ligating band and the second snare encircle the second portion of tissue; and
    repeating this process for each of a plurality of portions of tissue to be severed.

20. An apparatus for severing tissue within a living body via an endoscope extending from a proximal end to a distal end of the endoscope, comprising:
    a housing having a proximal end coupleable to a distal end of the endoscope, the housing defining an interior tissue receiving chamber and a ligating band supporting surface;
    at least one tissue snare which, in an operative configuration, is received around the ligating band supporting surface;
    a pull wire which, in an operative configuration, extends from a distal end of the pull wire coupled to the at least one tissue snare to a proximal end of the pull wire outside the living body; and
    at least one ligating band received around the ligating band supporting surface.

* * * * *